United States Patent [19]

Harmer

[11] 4,427,293

[45] Jan. 24, 1984

[54] DOUBLE OPTICAL PROBE DEVICE FOR THE DETERMINATION OF THE REFRACTIVE INDEX OF A LIQUID REDUCED TO A PREDETERMINED REFERENCE TEMPERATURE

[75] Inventor: Alan L. Harmer, Bernex, Switzerland

[73] Assignee: Battelle Memorial Institute, Carouge, Switzerland

[21] Appl. No.: 303,083

[22] Filed: Sep. 17, 1981

[30] Foreign Application Priority Data

Sep. 18, 1980 [CH] Switzerland ............... 6998/80

[51] Int. Cl.³ ............................................. G01N 21/41
[52] U.S. Cl. ..................................... 356/133; 356/136
[58] Field of Search ............... 356/128, 133, 135, 136, 356/137; 250/227

[56] References Cited

U.S. PATENT DOCUMENTS

| | | | |
|---|---|---|---|
| 2,984,148 | 5/1961 | Vollmer | 250/227 |
| 3,282,149 | 11/1966 | Shaw et al. | 356/130 |
| 3,520,619 | 7/1970 | Ward | 356/133 |
| 3,751,672 | 8/1973 | Michel et al. | 356/136 |
| 4,240,747 | 12/1980 | Harmer | 250/227 |

FOREIGN PATENT DOCUMENTS

476360  5/1929  Fed. Rep. of Germany ...... 356/133

Primary Examiner—R. A. Rosenberger
Attorney, Agent, or Firm—Karl F. Ross

[57] ABSTRACT

The device comprises two optical probes (51 and 52) consisting of a light conducting body which are designed to be immersed in the liquid by an intermediate section (53, 54) of the body, two light sources (60, 70) illuminating an extremity respectively of one (58) and of the other (68) body of the probes, two photoelectric transducers (61 and 72) located at the other extremity respectively of the first (58) and of the second (68) body of the probes, a member (73) which divides the signals originating from these transistors and a member (74) for the display of the resulting signal originating from that divider member.

6 Claims, 6 Drawing Figures

DOUBLE OPTICAL PROBE DEVICE FOR THE DETERMINATION OF THE REFRACTIVE INDEX OF A LIQUID REDUCED TO A PREDETERMINED REFERENCE TEMPERATURE

TECHNOLOGICAL FIELD OF APPLICATION

This invention relates to a double optical probe device for the determination of the refractive index of a liquid reduced to a predetermined reference temperature, said device being adapted to provide an error which is more positive than the negative error inherent to a single optical probe device (which thus provides, in particular, the possibility, when desired, to obtain an almost perfect temperature compensation, or even a certain overcompensation).

PREVIOUS ART

Many types of refractometers are known for the determination of the refractive index of liquids, a large number of which are based on the use of reflection and refraction phenomena occurring near the critical angle (the critical angle which is known to vary as a function of the refractive index of the liquid). Among the latter, immersion refractometers may be mentioned, in particular, which are measuring instruments in which simplicity and precision can be combined in a remarkable fashion. Such immersion refractometers generally include a single optical probe consisting of a light conducting structure designed to be immersed in the liquid to be meaured, which conducting structure is adapted to convey light through multiple internal reflections between the moment of entry and exit thereof by providing a passage of light by refraction through the liquid which is a function of the refractive index of that liquid (such conducting structures thus comprising, as an example, possibly, in particular, structures such as prisms located at the extremity of transparent rods, or structures such as simple transparent rods or optical fibers curved in an appropriate manner, etc.). The quantity of light transmitted up to the outlet of the optical probe comprising these immersion refractometers turns out, therefore, to be also a function of the refractive index of the liquid to be tested, so that the determination of this refractive index can thus be easily obtained by simple measurement of this quantity of light transmitted up to the outlet of the probe. To this effect, the outlet of the optical probe of these immersion refractometers is generally provided with a photoelectric converter designed to provide an electric signal corresponding to the quantity of light emerging at the outlet of the probe, this electric signal being then directed onto an appropriate display member directly calibrated in refractive index units, so as to provide for the direct reading of the required index value on this display member (the calibration of this display member being, as far as it is concerned, effected in a known manner at a well determined reference temperature, using standardization liquids the refractive index value of which at this predetermined reference temperature is known with precision).

It is known, however, that the refractive index "$n_l$" of practically all liquids decreases as the temperature increases, according to a temperature coefficient "$dn_l/dT$" which can range from approximately $-2 \times 10^{-4}/°C.$ to $-6 \times 10^{-4}/°C.$ depending on the liquids. Now, the result most generally looked for, in practice, as regards the determination of the refractive index of a given liquid, comprises the determination, whatever the actual temperature "T" at which this determination is carried out, of the value "$n_{lo}$" of the refractive index of this liquid reduced to a predetermined reference temperature "$T_o$" (generally, room temperature), rather than the actual value "$n_l$" of the refractive index of this liquid at the measurement temperature "T". This determination of the value "$n_{lo}$" of the refractive index reduced to a predetermined reference temperature "$T_o$" is indeed the only one that has an actual value in most applications, in particular, in all cases in which the determination of the refractive index of a given liquid is used, in fact, to provide for the determination of another characteristic "Q" of this liquid linked to its refractive index (taking into account the fact that the correlation existing between this characteristic "Q" and the refractive index is usually known by the user only for reference temperature $T_o$). A particularly advantageous application of this determination of the refractive index "$n_{lo}$" reduced to a predetermined reference temperature "$T_o$" comprises as a non limiting example, the determination of the state of charge "Q" of a storage battery such as an acid-lead battery, for which there is a well known correlation in the literature between this state of charge "Q" and the refractive index "$n_{lo}$" of the electrolyte in that battery at room temperature "$T_o$" ($T_o$ being set at 20° C.).

The use of single probe refractometers (such as described above) for the purpose of determining the refractive index "$n_{lo}$" of a given liquid reduced to a predetermined reference temperature "$T_o$", can only lead, consequently, as will shown in greater detail subsequently, to a result which is necessarily tainted with a highly negative error as soon as the temperature at which this determination is effected differs from the reference temperature (taking into account inevitable variations in the refractive index of the liquid to be tested as a function of temperature). This negative error inherent to such single probe refractometers turns out, in fact, where the refractive index of the transparent material comprising the probe is practically insensitive to temperature variations (for example, in glass where the refractive index has a temperature coefficient of the order of $-10^{-6}/°C.$, which value remains perfectly negligible with respect to that of most liquids), to be of a magnitude substantially equal to that of the temperature coefficient of the liquid to be tested, i.e., a magnitude of the order of $-2 \times 10^{-4}$ to $-6 \times 10^{-4}/°C.$ depending on the liquid tested (since the display member of the refractometer indicates, in fact, in such a case, the actual value $n_l$ of the refractive index shown by the liquid at the measuring temperature and not the value $n_{lo}$ of this index reduced to the reference temperature). It might be considered theoretically to substantially reduce or even almost completely cancel this negative error, by using as a solid transparent material comprising the probe, a material the refractive index of which has a temperature coefficient substantially equal to that of the liquid to be tested. Such a solid transparent material unfortunately does not exist in practice (solid transparent materials having the highest temperature coefficients consisting, indeed, of certain types of plastics the temperature coefficient of which exceeds by very little values of the order of $-1 \times 10^{-4}/°C.$), so that single probe refractometers used for the determination of the refractive index reduced to a predetermined reference temperature are inevitably tainted, for temperatures of use differing from that reference temperature, with a negative error the magnitude of which would not drop, whatever the material adopted, below a value of the order of $-1 \times 10^{-4}/°C$.

The only methods apparently advocated until now in order to nevertheless ensure a certain temperature compensation in such single probe refractometers are methods promoting the use of an additional system comprising a temperature measuring member such as a thermocouple associated to an electronic correction circuit, this complementary system being designed so that the electronic circuit can supply, as a function of the temperature recorded by the thermocouple, the required correction to the electric signal which is to be directed onto the display member of the refractometer. The necessity of using such an additional system is not, however, without a certain number of major drawbacks, such as: complexity of the electronic correction circuit; possible displacement between the respective thermal response times of the optical probe and the thermocouple (which may introduce an additional error when the refractive index to be tested varies as a function of time); possible difficulty in carrying out the temperature measurement with the thermocouple (for example, in environments in which there is a high electromagnetic interference), etc.

The object of this invention is precisely to remove, at least partially, the above mentioned drawbacks, by proposing a device with a double optical probe for the determination of the refractive index of a liquid reduced to a predetermined reference temperature, adapted so as to give rise to a error in said determination which is more positive than the negative error inherent to a device with a single optical probe. Such a solution thus provides, in particular, the possibility, according to desired applications, of obtaining an almost perfect temperature compensation (error in substantially reduced to zero), or even a certain temperature overcompensation (error made to be positive).

To this effect, this invention relates to a double optical probe device for the determination of the refractive index of a liquid reduced to a predetermined reference temperature, said device being adapted so as to give rise to an error which is more positive than the negative error inherent to a single optical probe device, characterized in that said device comprises:

a first and second optical probe each consisting of a light conducting body comprising an inlet section and an outlet section connected to each other by an intermediate section, at least said intermediate section of each of said probes being designed to be immersed in said liquid, and this intermediate section being, furthermore, adapted to convey light between said inlet section and said outlet section by giving rise to a quantity of light emerging from said outlet section of each of said probes which varies linearly as a function of the refractive index of said liquid, at least one source of light associated with said inlet section of said first and second probes designed to inject a predetermined quantity of light into each of these inlet sections, and means associated with said outlet section of said first and second probe, designed to elaborate a resulting signal corresponding to the difference in the quantities of light respectively emerging from said outlet sections, said intermediate sections of said first and second probes being, in addition, chosen, on the one hand, as regards their geometrical arrangement, so as to have respective sensitivities "$m_1$" and "$m_2$" relative to the variations in the refractive index of the liquid such that "$m_1$" is higher than "$m_2$" and, on the other hand, as regards the material comprising them, so as to have respective apparent sensitivities "$q_1$" and "$q_2$" relative to the variations in temperature of this liquid such that "$q_1$" is lower than "$q_2$", so that said resulting signal elaborated at the outlet of said probes constitutes a signal which is representative of said refractive index of the liquid reduced to said reference temperature, the refractive index thus determined being, furthermore, tainted, for temperatures differing from this reference temperature, with an error in temperature which is more positive than that which might result from the use of a single probe.

This invention also relates to a double optical probe device for the determination of the refractive index of a liquid reduced to a predetermined reference temperature, said device being adapted to give rise to an error which is more positive than the negative error inherent to a single optical probe device, characterized in that said optical probe device comprises:

a first and second optical probe each consisting of a light conducting body comprising an inlet section and an outlet section connected to each other by an intermediate section, at least said intermediate section of each of said probes being designed to be immersed in said liquid, and this intermediate section being, furthermore, adapted to convey light between said inlet section and said outlet section by giving rise to a quantity of light emerging from said outlet section of each of said probes which varies exponentially as a function of the refractive index of said liquid, at least one source of light associated with said inlet section of said first and second probes, designed to inject a predetermined quantity of light into each of these inlet sections, and means associated to said outlet section of said first and second probes, for the elaboration of a resulting signal corresponding to the quotient of the quantities of light respectively emerging from said outlet sections, said intermediate sections of said first and second probes being, in addition, chosen, on the one hand, as regards their geometric arrangement, so as to have respective exponentiality coefficients "$k_1$" and "$k_2$" relative to the variations in the refractive index of the liquid which are such that "$k_1$" is higher than "$k_2$", and, on the other hand, as regards the constituent material thereof, so as to have apparent respective sensitivities "$q_1$" and "$q_2$" relative to the variations in temperature of this liquid which are such that "$q_1$" is lower than "$q_2$", so that said resulting signal elaborated at the outlet of said probes constitutes a signal which is representative of said refractive index of the liquid reduced to said reference temperature, the refractive index thus determined being, furthermore, tainted, for temperatures differing from this reference temperature, with an error which is more positive than that which would result from the use of a single probe.

In the double optical probe devices such as defined above, the general expression "light conducting body comprising an inlet section and an outlet section connected to each other by an intermediate section" is intended to mean any optical structure which can convey light by multiple internal reflections from the inlet section to the outlet section of that structure. Such an expression is thus intended, in particular, to encompass structures that are as diverse as structures the intermediate section of which consists of a prismatic surface (the inlet and outlet sections connected to this prismatic surface then possibly consisting, for example, of longilinear light conducting bodies such as transparent rods or optical fibers), or structures consisting entirely of longilinear light conducting bodies (such as transparent rods or optical fibers).

In the double optical probe devices such as defined above, the general expression "means for the elaboration of a corresponding signal resulting from the difference or the quotient of quantities of light emerging from the respective probes of the double probe device" is intended, furthermore, to refer to both purely optical means giving rise to the elaboration of a resulting optical signal (the difference or the quotient of quantities of light emerging from the respective probes being then obtained by purely optical means) and "optoelectronic" means giving rise to the elaboration of a resulting electric signal (the quantities of light emerging from the respective probes being then preferentially converted into corresponding electric signals through appropriate means such as photoelectric converters, so as to provide for subsequent elaboration, using appropriate electronic means, of the difference or of quotient of these respective electric signals, using appropriate electronic means).

BRIEF DESCRIPTION OF THE DRAWINGS

The appended drawing shows, schematically, and as an example, two embodiments of the device, which is the object of this invention.

BETTER WAYS OF IMPLEMENTING THE INVENTION

Figure 1A:
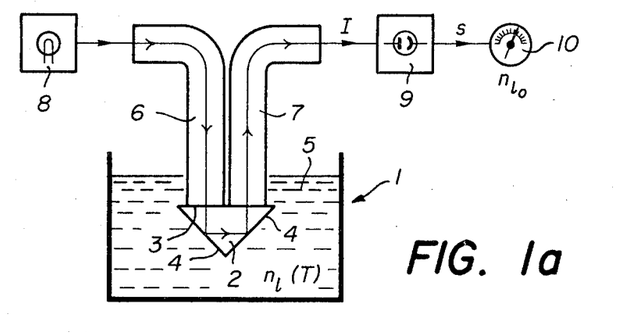
FIGS. 1a and 1b are schematic longitudinal sectional views, illustrating two single optical probe devices known from the state of the art.
Figure 1B:
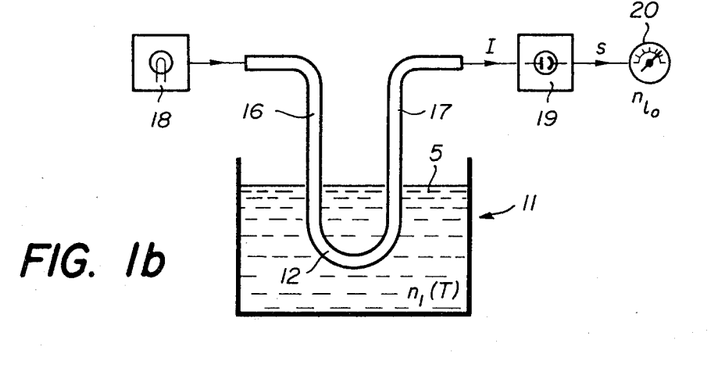
Figures 2A, 2B:
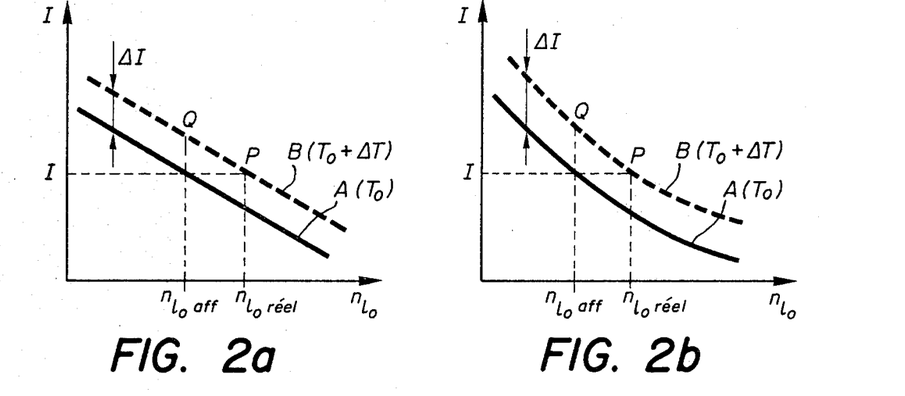
FIGS. 2a and 2b are diagrams illustrating the error relating to the devices of FIGS. 1a and 1b.

FIGS. 1a and 1b illustrate, as an example, two single optical probe devices known from the state of the art, designed to provide for the determination of the refractive index "$n_o$" of a liquid reduced to a predetermined reference temperature "$T_o$" (the mode of operation of these devices being, furthermore, illustrated by the diagrams in FIGS. 2a and 2b). These first two illustrations are designed to show with what error the determination thus carried out with these known single probe devices is tainted, when the temperature T at which this determination is effected differs from the reference temperature $T_o$, so as to provide for the establishment of a precise comparison with the error which may result from the use of double optical probe devices according to the invention which will be described subsequently.

The device shown in FIG. 1a comprises a single optical probe 1, consisting of a prism 2 having a base 3 and two other faces 4 inclined at the same angle with respect to base 3. Prism 2, which is made of a transparent material with a refractive index "$n_p$" is immersed in a liquid to be tested 5 having a refractive index of "$n_f$" (the respective refractive indices "$n_p$" and "$n_f$" varying as a function of temperature "T" prevailing at the time of measurement). Optical probe 1 comprises two other light conductors 6 and 7 rigidly connected by one of their extremities to face 3 of prism 2, which are designed to act respectively as an inlet section and an outlet section for the probe. Opposite the free extremity of inlet section 6 of probe 1, is located a light source 8, which is designed to inject a predetermined quantity of light inside probe 1. The light thus injected at the inlet of probe 1 is then conveyed to the outlet of the latter after having undergone two successive reflections on the inclined faces 4 of prism 2 immersed in the liquid to be tested 5. These two successive reflections on the faces of the prism give rise, as is known, to a passage of light by refraction in liquid 5 which is a function of the refractive index of that liquid, so that the quantity of light "I" transmitted up to the outlet of the probe turns out also to be a function of that refractive index. Opposite section 7 of probe 1, is further located a photoelectric transducer 9 designed to elaborate an electric signal "s" representing this quantity of light "I" emerging from outlet section 7 (transducer 9 being in fact chosen so that the elaborated signal "s" is directly proportional to the quantity "I", in accordance with the relation s=αI, where α represents the coefficient of proportionality). Finally, photoelectric transducer 9 is connected to a display member 10, designed to display directly the value of the refractive index "$n_{eo}$" of the liquid tested 5, reduced to the predetermined reference temperature "$T_o$" (this predetermined reference temperature "$T_o$" being possibly, as an example, room temperature set at 20° C.).

In order to provide for the above-mentioned display, display member 10 is calibrated directly in refractive index units, this calibration being carried out at the reference temperature "$T_o$" using standardizing liquids the index values of which "$n_{lo}$" are known with precision at that temperature "$T_o$". Such a calibration or standardization is more clearly illustrated by curve A shown as a solid line in the diagram of FIG. 2a, which shows the variations in the quantity of light "I" transmitted by probe 1 as a function of the refractive index "$n_{lo}$" of the standardization liquids maintained at the reference temperature $T_o$. It is noted that the special nature of probe 1 (consisting of a prism 2) gives rise to a transmitted quantity of light "I" which varies linearly as a function of the index "$n_{lo}$", this linear variation I ($n_{lo}$) being expressed by the relation:

$$I = f(n_{lo}) = C = (mn_{lo})$$

where "C" is a constant, and "m" is the slope "$dI/dn_{n_o}$" of straight line A, this parameter "m" representing, in fact, the sensitivity of probe 1 with respect to the variations of the refractive index of the liquid to be tested.

The device described being thus calibrated, its operation is as follows: with prism 2 of probe 1 comprising this device immersed in an unknown liquid the refractive index "$n_{lo}$" of which reduced to the reference temperature "$T_o$" is to be determined, injection of a predetermined quantity of light at the inlet of probe 1 gives rise to a quantity of light "I" transmitted at the outlet of this probe which is converted to a display having a value "$n_{lo}$ disp" on the display member 10 (see standardizing curve A shown in the diagram of FIG. 2a, where this value "$n_{lo}$" is given by the abscissa of point O of curve A the ordinate of which consists of the value "I" thus elaborated by the probe). This value "$n_{lo}$ disp."

corresponds indeed to the actual value "$n_{lo}$ act." required when the temperature T of the probe 1-liquid 5 system is equal to the reference temperature $T_o$. This value "$n_{lo}$ disp." is, on the other hand, substantially different from the value "$n_{lo}$ act." required when the temperature T of the system turns out to be no longer equal to the reference temperature $T_o$, the error in temperature E thus made on the determination of the index "$n_{lo}$" reduced to the reference temperature $T_o$ being then given by the relation:

$$E = \frac{n_{lo} \text{ act.} - n_{lo} \text{ disp.}}{\Delta T}$$

where $\Delta T$ denotes the deviation between the temperature of measurement T and reference temperature $T_o$.

This error E can easily be calculated from the diagram of FIG. 2a, by including in this diagram, straight line B (drawn as a dotted line) representing the variation of the quantity of light "I" actually transmitted by probe 1 at temperature T as a function of variations of index "$n_{lo}$" of the liquid reduced to reference temperature $T_o$, which variation obeys the following relation:

$$I = f(n_{lo}) + \frac{dI}{dT} \Delta T = C - (m \cdot n_{lo}) + \frac{dI}{dT} \Delta T$$

where dI/dT is the derivative of the value I as a function of the temperature T.

It noted then that straight line B is a straight line translated from standardizing straight line A by a value $\Delta I$ such that:

$$\Delta I = (dI/dT)\Delta T$$

The actual value "$n_{lo}$ act." required is thus given in the diagram of FIG. 2a by the abscissa of point P of curve B the ordinate of which always consists of the value "I" elaborated by the probe at temperature I, so that the error E can then be written as follows:

$$E = \frac{n \text{ act.} - n_{eo} \text{ disp.}}{\Delta T} = \frac{OP}{\Delta T}$$

or also, by considering that $OQ = \Delta I$ and the $OQ/OP = -$ the slope of straight lines A and $B = dI/dn_{lo}$:

$$E = dI/dT/dI/dn_{lo}$$

The derivative dI/dT must now be calculated in order to determine the value E as a function of the parameters of the probe 1-liquid 5 system.

It is known that in any optical probe designed to determine the refractive indices "$n_l$" of a liquid, the quantity of light "I" transmitted by the probe is a function of the refractive index "$n_p$" of the probe and of the refractive index "$n_l$" of the liquid (the indices "$n_p$" and "$n_l$" being themselves a function of the temperature T of the system), in accordance with the relation:

$$I = f(n_l/n_p)$$
$$= f[n_l(T)/n_p(T)]$$

The derivative $dI/dn_l$, which constitutes, as indicated above, the sensitivity "m" of the probe in relation to variations in the refractive index of the liquid, can then be written as follows (with $z = n_l/n_p$):

$$dI/dn_l = m = \left( \frac{1}{n_p} \cdot \frac{df}{dz} \right)$$

The derivative dI/dT, which constitutes an indicator of the dependence of the system on temperature, can, as far as it is concerned, be written as follows:

$$\frac{dI}{dT} = \frac{d}{dT} [n_l(T)/n_p(T)]$$

$$\frac{dI}{dT} = \frac{1}{n_p} \left( \frac{dn_l}{dT} - \frac{n_l}{n_p} \cdot \frac{dn_p}{dT} \right) \left( \frac{df}{dz} \right)$$

Let us write as an arbitrary definition:

$$\left[ \frac{dn_l}{dT} - \frac{n_l}{n_p} \frac{dn_p}{dT} \right] = q$$

by agreeing to have "q" stand for the sensitivity of the probe with respect to temperature variations T.

Derivatives dI/dT and $dI/dn_l$ being thus calculated, it can be seen that the error E such as defined above can then be expressed as follows as a function of the parameters of the system:

$$E = \left[ \frac{dn_l}{dT} - \frac{n_l}{n_p} \frac{dn_p}{dT} \right] = q$$

It is noted then, in conclusion, that this error E always remains negative for single probe devices, taking into account the fact that the temperature coefficients "dn/dT" of most liquids have a value which varies from approximately $-2 \times 10^{-4}$ to $-6 \times 10^{-4}/°C$. depending on the liquids, whereas the temperature coefficients "$dn_p/dT$" of practically all solid transparent materials have values which are generally much lower. This negative error E turns out to be a maximum for single probe devices the constituent material of which is glass (having a temperature coefficient of the order of $10^{-6}/°C$., which is negligible as compared with that of liquids). This negative error E may be substantially reduced through the use, as a constituent material of the probes, of materials such as certain plastics having the highest known temperature coefficients (of the order of $1 \times 10^{-4}/°C$.). Such a negative temperature error can nevertheless at most be reduced only (without, however, being able to come down much below a value of the order of $1 \times 10^{-4}/°C$.), but not cancelled and even less be made positive.

The device shown in FIG. 1b comprises a single probe 11, consisting of a U-shaped optical fiber comprising a semicircular curved section 12 extending at each of its extremities by respective right sections 16 and 17. Curved section 12 of fiber 11, the heart of which is made of a material having a refractive index of "$n_p$", is immersed in a liquid to be tested 5 having a refractive index "$n_l$" (the respective refractive indices "$n_p$" and "$n_l$" varying as a function of the temperature of measurement "T"). Opposite the free extremity of the inlet section 16 of fiber 11, is a light source 18, designed to inject a predetermined quantity of light inside fiber 11. The light thus injected at the inlet of fiber 11 is then conveyed up to the outlet of the latter while giving rise, as is known, to losses of light through refraction at the curvature, which are a function of the refractive index of the liquid (a curvature of curved section 12 chosen to be sufficiently pronounced in order for these losses not to be negligible), so that the quantity of light "I" emerging at the outlet of fiber 11 turns out also to be a function of the refractive index of that liquid. Opposite the outlet of fiber 11, there is, furthermore, a photoelectric transducer 19, which is designed to elaborate an electric signal "s" which is directly proportional to this quantity of light "I" emerging from fiber 11. The photoelectric transducer 19 is finally connected to a display member 20, the function of which is to supply directly the value of the refractive index "$n_{lo}$" of the liquid tested 5 reduced to the reference temperature $T_o$. To this effect, the display member is directly calibrated in refractive index units, this calibration being, furthermore, operated as previously at reference temperature $T_o$, using standardizing liquids the index values of which "$n_{lo}$" are known with precision at this temperature "$T_o$". Such a calibration or standardization is more clearly illustrated by curve A shown in the diagram of FIG. 2b, which shows the variations in the quantity of light "I" transmitted by fiber 11 as a function of the refractive index "$n_{lo}$" of the standardization liquids maintained at the reference temperature "$T_o$". It is noted in this diagram that the special nature of the probe used (i.e., a curved optical fiber) gives rise to a quantity of transmitted light "I" which varies exponentially as a function of index "$n_{lo}$", this exponential variation I ($n_{lo}$) being expressed by the relation:

$$I = f(n_{lo}) = Ce^{-kn_{lo}}$$

where "C" is a constant and "k" is the exponentiality coefficient of the probe in relation to the variations in the refractive index of the liquid to be tested.

The device described above makes it possible to determine, as done previously, the refractive index "$n_{lo}$" of an unknown liquid reduced to the reference temperature "$T_o$", this determination also giving rise, when the temperature of measurement T is different from reference temperature "$T_o$", to an error E which can be expressed as previously by the relation (see diagram FIG. 2b):

$$E = \frac{n_{lo}\, act. - n_{lo}\, disp.}{\Delta T} = \frac{dI/dT}{dI/dn_{lo}}$$

The quantity of light "I" transmitted by optical probe 11 is, furthermore, as previously, always a function of the refractive index "$n_p$" of the probe and of the refractive index "n" of the liquid, in accordance with the relation:

$$I = f[n_l(T)/n_p(T)]$$

so that the derivative dI/dT can always be written as follows:

$$\frac{dI}{dT} = \frac{dI}{dn}\left[\frac{dn_l}{dT} - \frac{n_l}{n_p}\frac{dn}{dT}p\right]$$

The expression of the error in temperature E as a function of the parameters of the system then turns out, in conclusion, to be strictly identical with that given previously, i.e.;

$$E = \left[\frac{dn_l}{dT} - \frac{n_l}{n}\frac{dn_p}{dT}\right] = q$$

which error E then always remains negative.

Figure 3:
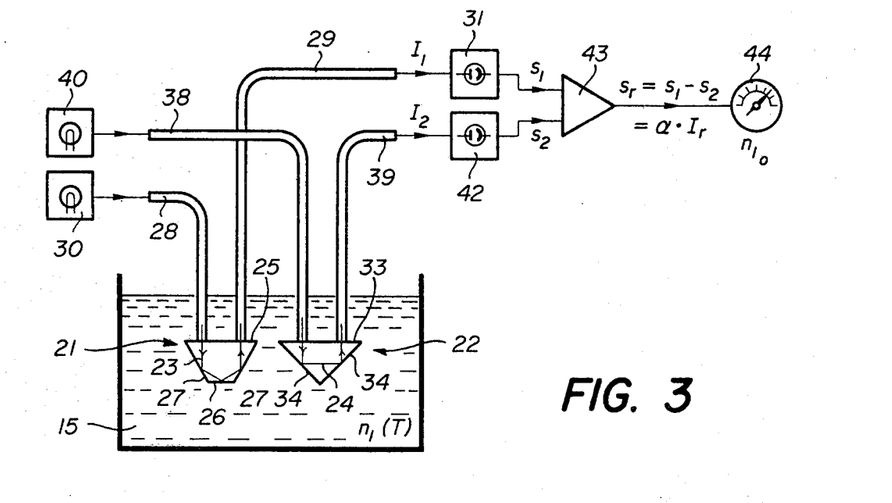
FIG. 3 is a longitudinal sectional view similar to that of FIGS. 1a and 1b, illustrating a first embodiment of the double optical probe device according to the invention.

FIG. 3 illustrates a first mode of application of the double optical probe device according to the invention, characterized in that optical probes with linear characterisics I ($n_l$) are used.

The device shown in this FIG. 3 comprises two optical probes 21 and 22, consisting of respective prisms 23 and 24 made of transparent materials having respective refractive indices "$n_{p1}$" and "$n_{p2}$", said prisms 23 and 24 being, furthermore, immersed in a liquid to be tested 15 having a refractive index "$n_l$".

Prism 23 of the first optical probe 21 comprises a base 25 which is larger than an opposite parallel face 26, as well as two other faces 27 inclined by the same angle with respect to base 25. The first optical probe 21 comprises, furthermore, two light conductors 28 and 29 rigidly connected through one of their extremities to the base 25 of prism 23, which are designed to act respectively as an inlet section and an outlet section for probe 21. Opposite the free extremity of inlet section 28 of probe 21, there is a first light source 30, the function of which is to inject a predetermined quantity of light inside probe 21, while opposite the outlet section 29, there is a first photoelectric transducer 31, designed to elaborate an electric signal "$s_1$" which is directly proportional to the quantity of light "I" transmitted up to the outlet of this first probe 21 (light transmitted up to the outlet of probe 21 after having undergone three successive reflections on the corresponding faces 26 and 27 of prism 23).

Prism 24 of the second optical probe 22 comprises, as far as it is concerned, a base 33, as well as two other faces 34 inclined by the same angle with respect to this base 33. The second optical probe 22 comprises, furthermore, two light conductors 38 and 39 rigidly connected through one of their extremities to the base 33 of prism 24, which are designed to act respectively as an inlet section and an outlet section for probe 29. Opposite the free extremity of inlet section 38 of outlet 27, there is a second light source 40 which is designed to inject a predetermined quantity of light inside probe 22, while opposite outlet section 39, there is a second photoelectric transducer 42, designed to elaborate an electric signal "$s_2$" which is directly proportional to the quantity of light "$I_2$" transmitted up to the outlet of this second probe 22 (light transmitted up to the outlet of probe 22 after having undergone two successive reflections on the corresponding faces 34 of prism 24).

The special geometric arrangement of each of prisms 23 and 24 as described above (prism 23 comprising three reflecting surfaces, while prism 22 has only two) was specifically chosen so as to give rise, for reasons which will be explained below, to a sensitivity "$m_1$" for the first probe 21 ("$m_1$" being such that $m_1 = dI_1/dn_l$) which is greater than the sensitivity "$m_2$" relative to the second probe 22 ("$m_2$" being such that $m_2 = dI_2/dn_l$).

The outlets of photoelectric transducers 31 and 42 associated with probes 21 and 22 are, furthermore, connected to both inlets of a differentiating member 43, designed to elaborate a resulting electric signal "$s_1$"

corresponding to the difference between signals "$s_1$" and "$s_2$". Taking into account the proportionality coefficient "$a$" between the respective signals "$s_1$" and "$s_2$" and the respective values "$I_1$" and "$I_2$", the resulting signal "$s_r$" can then be written indifferently as follows:

$$s_r = (s_1 - s_2)$$
$$= a(I_1 - I_2)$$

or even as $s_r = aI_r$ choosing by convention $I_r$ as the difference between the quantities $I_1$ and $I_2$.

The outlet of differentiating member 43 is finally connected to a display member 44, designed to directly display the value of the refractive index "$n_{lo}$" of the liquid tested 15 reduced to the predetermined reference temperature "$T_o$". To this effect, display member 44 is directly calibrated in refractive index units, this calibration being carried out (as for single probe devices) at the reference temperature $T_o$, using standardization liquids the index values of which "$n_{lo}$" at this temperature "$T_o$" are known with precision (the value "$s_r$" or "$dI_r$" being indeed representative of the index "$n_{lo}$" at the reference temperature "$T_o$", since the values comprising "$s_1$" and "$s_2$" are already representative of this index "$n_{lo}$" at the temperature "$T_o$", as noted previously).

With the device described above thus calibrated, its mode of operation is then as follows: as prisms 23 and 24 of the respective probes 21 and 22 are immersed in the liquid the refraction index "$n_{lo}$" of which, reduced to the reference temperature "$T_o$", is to be determined, the injection of a predetermined quantity of light at the inlet of probes 21 and 22 then gives rise to respective quantities of light "$I_1$" and "$I_2$" at the outlet of these probes which give rise, after elaboration of the resulting signal "$aI_r$", to the display of a value "$n_{lo}$ disp." on the display member 44. This displayed value "$n_{lo}$ disp." corresponds indeed to the actual value "$n_{lo}$ act." required, when the temperature T of the system is equal to the reference temperature $T_o$. This value "$n_{lo}$ disp." may, on the other hand, no longer be equal to the value "$n_{lo}$ act." required, when the temperature T of the system differs from reference temperature $T_o$, the error E which may thus be made with regard to the determination of the index "$n_{lo}$" reduced to $T_o$ being then given (in a manner similar to that shown above) by the relation:

$$E = \left[ \frac{n_{lo} \text{ act.} - n_{lo} \text{ disp.}}{\Delta T} \right] = \frac{dI_r/dT}{dI_r/dn_{lo}}$$

The respective derivatives $dI_r/dT$ and $dI_r/dn$ can now be calculated so as to determine the value of error E as a function of the parameters of the system.

As shown previously, the quantities of light "$I_1$" and "$I_2$" transmitted by the respective probes 21 and 22 can be expressed using the following relations:

$$I_1 = C_1 - (m_1 n_{lo}) + \frac{dI}{dT} 1 \, \Delta T$$
$$= C_1 - (m_1 n_{lo}) - m_1 q_1 \, \Delta T$$

and $$I_2 = C_2 - (m_2 n_{lo}) + \frac{dI}{dT} 2 \, \Delta T$$

$$= C_2 - (m_2 n_{lo}) - m_2 q_2 \cdot \Delta T$$

where

"$C_1$" and "$C_2$" are constants,

"$m_1$" and "$m_2$" the respective sensitivities "$dI_1/dn_{lo}$" and

"$dI_2/dn_{lo}$" of probes 21 and 22 relative to the variations of the refractive index of the liquid to be tested, and, "$q_1$" and "$q_2$" the apparent respective sensitivities of probes 21 and 22 relative to the temperature variations of the system with:

$$q_1 = \left[ \frac{dn_l}{dT} - \frac{n_l}{n_{p1}} \frac{dn}{dT} p1 \right]$$

and $$q_2 = \left[ \frac{dn_l}{dT} - \frac{n_l}{n_{p2}} \frac{dn}{dT} p2 \right]$$

The resulting value $I_r$ can then be rewritten as follows:

$$I_r = (I_1 - I_2)$$
$$= (C_1 - C_2) - (m_1 - m_2) n_{lo} - (m_1 q_1 - m_2 q_2) \Delta T$$

from which the following respective derivatives are obtained:

$$\frac{dI_r}{dT_{lo}} = -(m_1 q_1 - m_2 q_2)$$

and $$\frac{dI_r}{dn_{lo}} = -(m_1 - m_2)$$

which then gives the following relation for the error E:

$$E = \frac{dI_r/dT}{dI_2/dn_{lo}} = \frac{m_1 q_1 - m_2 q_2}{m_1 - m_2}$$

The condition in order for this error E to be made more positive than the negative error "$q_1$" or "$q_2$" which might inevitably result from the use of probe 21 alone or of probe 22 alone is then that:

$$\frac{m_1 q_1 - m_2 q_2}{m_1 - m_2} < q_1 \text{ or } q_2$$

Taking into account that respective probes 21 and 22 were chosen with regard to their geometric arrangement so that "$m_1$" would be greater than "$m_2$", the condition stated above is thus satisfied when "$q_1$" is chosen to be lower than "$q_2$". This condition, namely that "$q_1$" < "$q_2$" implies, as regards the constituent materials of prisms 23 and 24 of respective probes 21 and 22, the simple choice, for the prism of the first probe 21, of a transparent material with an index "$n_{p1}$" the temperature coefficient of which "$dn_{p1}/dT$" is greater than the temperature coefficient "$dn_{p2}/dT$" of the transparent material with an index "$n_{p2}$" chosen for the prism of the second probe 24. Such a condition, namely $q_1<q_2$ can thus, as an example, be easily satisfied by choosing, respectively, a material such as polystyrene ($dn_{p1}/dT = -1\times 10^{-4}/°C$.) as a constituent material of prism 23 of the first probe 21 and a material such as glass ($dn_{p2}/dT = -1\times 10^{-6}/°C$.) for prism 24 of the second probe 22.

If both probes have prisms 24 and 25 with the same shapes and dimensions so that their sensitivities $m_1$ and $m_2$ are substantially equal, it will be convenient to choose photodetectors having a characteristic such that the proportionality of each probe, 1 and 2, is different from one probe to the next. It follows that it will be possible to obtain an effect identical to that previously described in the case of prisms 24 and 25 having a different shape by acting only on the sensitivity of the photodetectors.

Summarizing, it can be noted, therefore, that the double optical probe device such as described above provides for the determination of the refractive index "$n_{lo}$" of a liquid reduced to the reference temperature $T_o$, in accordance with an error E which turns out to be more positive than the negative error inherent to the use of a single probe device, whenever the following conditions are satisfied:

$$m_1 > m_2$$

and $$q_1 < q_2 \text{ (or } dn_{p1}/dT > dn_{p2}/dT)$$

This error E can, however, be practically cancelled by choosing the respective parameters $m_1$, $m_2$, $q_1$ and $q_2$ so that they obey the relation:

$$m_1 q_1 \approx m_2 q_2$$

which then makes it possible to obtain a measuring device which is seen to be almost perfectly temperature compensated.

This error E can, in addition, in certain desired cases, be made to be positive through an appropriate choice of the respective parameters $m_1$, $m_2$, $q_1$ and $q_2$, which then makes it possible to obtain a temperature overcompensated device (which is impossible with single probe devices). Such a possibility for temperature overcompensation can actually be particularly advantageous in a certain number of applications, such as for example that which is directed towards the determination of the state of charge Q of an acid-lead battery through the measurement of the refractive index "$n_{lo}$" of its electrolyte reduced to the reference temperature $T_o$ (such an overcompensation thus making it possible, as an example, to indicate to the driver of a vehicle, in cold weather, a charge "Q disp." which is substantially lower than the actual charge "Q act." of his battery, so as to increase safety in usage).

Figure 4:
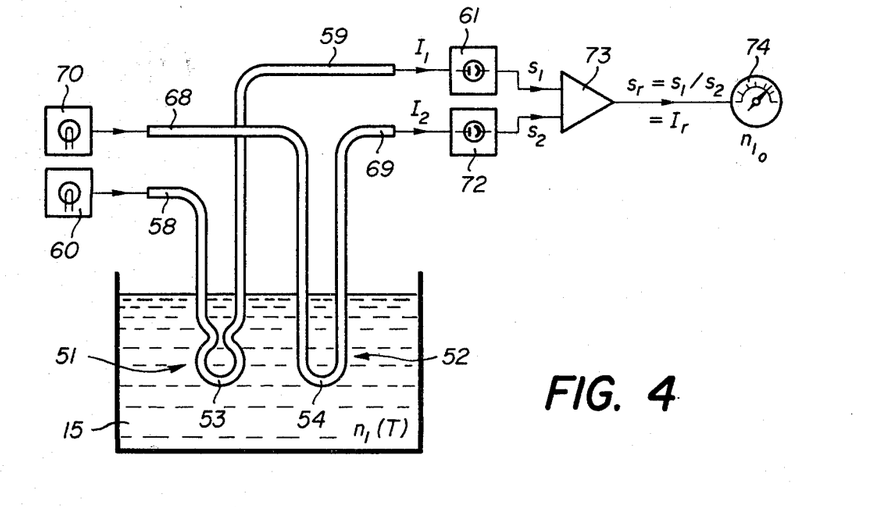
FIG. 4 is a longitudinal sectional view similar to that of FIG. 3, illustrating a second embodiment.

FIG. 4 illustrates a second mode of application of the double optical probe device according to the invention, characterized in that optical probes with exponential characteristic I ($n_{lo}$) are used.

The device shown in this FIG. 4 comprises two optical probes 51 and 52, consisting of curved optical fibers the heart of which is made of transparent materials having a respective refractive index "$n_{p1}$" and "$n_{p2}$", the curved sections 53 and 54 of these optical fibers 51 and 52 being, furthermore, immersed in the liquid to be tested 15 having a refractive index "$n_l$".

The curved section 53 of the first fiber 51 has an "inverted Ω" shaped profile comprising three alternate curvatures. This curved section 53 extends to each of its extremities by respective right sections 58 and 59, which are designed to act respectively as an inlet section and as an outlet section for probe 51. Opposite the free extremity of inlet section 58 of probe 51, there is a first light source 60, the function of which is to inject a predetermined quantity of light inside probe 51, while opposite outlet section 59, there is a first photoelectric transducer 61, designed to elaborate an electric signal "$s_1$" which is directly proportional to the quantity of light "$I_1$" transmitted up to the outlet of this first probe 61 (light transmitted up to the outlet of probe 51 after having undergone losses through refraction on the three successive inverted curvatures of curved section 53).

Curved section 54 of the second fiber 52 has, as far as it is concerned, a profile with a single U-shaped curvature. This curved section 54 extends to each of its extremities by right respective sections 68 and 69, which are designed to act as an inlet section and as an outlet section for probe 52. Opposite the free extremity of inlet section 68 of probe 52, there is a second light source 70, the function of which is to inject a predetermined quantity of light inside section 52, while opposite outlet section 69, there is a second photoelectric transducer 72, the function of which is to elaborate an electric signal "$s_2$" which is directly proportional to the quantity of light "$I_2$" transmitted up to the outlet of this second probe 52 (light transmitted up to the outlet of probe 52 after having undergone losses through refraction during its passage through the single curvature 54).

The special geometric arrangement of the respective curved sections 53 and 54 such as described above (section 53 comprising three inverted curvatures, while section 54 comprises only one) was specifically chosen so as to give rise, for reasons which will be explained below, to an exponentiality coefficient "$k_1$" for the first probe 51 which will be greater than the exponentiality coefficient "$k_1$" relative to the second probe 52.

The outlets of photoelectric transducers 61 and 72 associated with respective probes 51 and 52 are, furthermore, connected to the two inlets of a dividing member 73, the function of which is to elaborate a resulting electric signal "$s_r$" corresponding to the quotient of signals "$s_1$" and "$s_2$". Taking into account the proportionality coefficient "α" between the respective signals "$s_1$" and "$s_2$" and the respective values "$I_1$" and "$I_2$", the resulting signal "$s_r$" can then be written indifferently:

$$s_r = s_1/s_2$$
$$= I_1/I_2 = I_r$$

by choosing $I_r$ as the quotient $I_1/I_2$.

The outlet of divider member 73 is finally connected to a display member 74, the function of which is to display directly the value of the refractive index "$n_{lo}$" of the liquid tested 15 reduced to the predetermined reference temperature "$T_o$". To this effect, display member 74 is calibrated directly in refractive index units, this calibration being effected (as for the single probe devices) at the reference temperature $T_o$, using standardization liquids the index values "$n_{lo}$" of which are known with precision at this temperature "$T_o$" (the value "$s_r$" or "$l_r$" being indeed representative of the index "$n_{lo}$" at the reference temperature "$T_o$", since the component values "$s_1$" and "$s_2$" are already representative of this index "$n_{lo}$" at the temperature "$T_o$", as seen previously).

With the above-described device calibrated, its mode of operation is then as follows: as the curved sections 53 and 54 of the respective probes 51 and 52 are immersed in the liquid the refractive index "$n_{lo}$" of which, reduced to the reference temperature "$T_o$", is to be determined, the injection of a predetermined quantity of light at the inlet of probes 51 and 52 then gives rise to respective quantities of light "$I_1$" and "$I_2$" at the outlet of the probes, which give rise, after elaboration of the resulting signal "$I_r$", to the display of a value "$n_{lo}$ disp." on the display member 74. This displayed value "$n_{lo}$" indeed corresponds to the actual value "$n_{lo}$ act." required, when the temperature T of the system is equal to the reference temperature $T_o$. This value "$n_{lo}$ disp." may, on the other hand, no longer be equal to the required value "$n_{eo}$ act.", when the temperature T of the system differs from the reference temperature $T_o$, the error E which may thus be apportioned to the determination of the index "$n_{lo}$" reduced to $T_o$ being then given (in a manner similar to that shown above) by the relation:

$$E = \frac{n_{lo} \text{ act.} - n_{lo} \text{ disp.}}{\Delta T} = (dI_r/dT)/(dI_r/dn_{lo})$$

The respective derivatives $dI_r/dT$ and $dI_r/d_n$ can now be calculated in order to determine the value of error E as a function of the parameters of the system.

As shown previously, the quantities of light "$I_1$" and "$I_2$" transmitted by the respective probes 51 and 52 can be expressed using the following relations:

$$I_1 = C_1 e^{-k_1 nl} + \frac{dI_1}{dT} \Delta T$$

and $$I_2 = C_2 e^{-k_2 nl} + \frac{dI_2}{dT} \Delta T$$

or still, taking into account that $dI/dT = q_1 dI/dn$, with $dI/dn = kI$ (for probes with an exponential characteristic):

$$I_1 = C_1 e^{-k_1 n} 1 - k_1 q_1 \Delta T$$

and $$I_2 = C_2^{-k_2 n} 1 - k_2 q_2 \Delta T$$

where "$C_1$" and "$C_2$" are constants,

"$k_1$" and "$k_2$" the respective exponentiality coefficients of probes 51 and 52 in relation to the variations of the index of the liquid to be tested, and, "$q_1$" and "$q_2$", the respective apparent sensitivities of probes 51 and 52 relative to the variations in temperature of the system with:

$$q_1 = \frac{dn_l}{dT} - \frac{n_l}{n_{p1}} \frac{d_{p1}}{dT}$$

and $$q_2 = \frac{dn_l}{dT} - \frac{n_l}{n_{p2}} \frac{d_{p2}}{dT}$$

The resulting value $I_r$ can therefore be written as follows:

$$I_r = I_1/I_2$$

$$= \frac{C_1 e^{-(k_1-k_2)nl}}{C_2} \frac{1 - k_1 q_1 \Delta T}{1 - k_2 q_2 \Delta T}$$

or still as follows:

$$I_r = (C_1/C_2) e^{-(k_1-k_2)nl} [1 - (k_1 q_1 - k_2 q_2 \Delta T]$$

by assuming that the quantities $K_1 q_1 \Delta T$ and $k_2, q_2, \Delta T$ remain infinitely small with respect to unity (which is verified in practice).

The following respective derivatives are then obtained:

$$dI_r/dT = -(k_1 q_1 - k_2 q_2) I_r$$

and $$dI_r/dn_{lo} = -(k_1 - k_2) I_r$$

which then leads to the following relation for the error E:

$$E = \frac{dI_r/dT}{dI_r/dn_{lo}} = \frac{k_1 q_1 - k_2 q_2}{k_1 - k_2}$$

The condition for that error E to be made more positive than the negative error "$q_1$" or "$q_2$" which might inevitably result from the use of probe 51 alone or of probe 52 alone is therefore that:

$$\frac{k_1 q_1 - k_2 q_2}{k_1 - k_2} < q_1 \text{ or } q_2$$

Taking into account the fact that the respective probes 51 and 52 were chosen as regards their geometric arrangement so that "$k_1$" is greater than "$k_2$", the above-mentioned condition is thus satisfied when "$q_1$" is chosen to be lower than "$q_2$". This condition, namely that "$q_1$" < "$q_2$" implies, as regards the constituent materials of the hearts of the respective fibers 51 and 52, the simple choice for the heart of the first fiber 51 of a transparent material with an index "$n_{p1}$" the temperature coefficient of which "$dn_{p1}/dT$" is greater than the temperature coefficient "$dn_{p1}/dT$" of the transparent material having an index "$n_{p2}$" chosen for the heart 33 of the second fiber 54. Such a condition, namely that $q_1 < q_2$, can thus, as an example, be easily satisfied by choosing, respectively, a material such as polystyrene ($dn_{p1}/dT = -1 \times 10^{-4}/°C$.) as a constituent material of the heart of the first probe 51, and a material such as glass ($dn_{p2}/dT = -1 \times 10^{-6}/°C$.) for the heart of the second probe 52.

Summarizing, it can therefore be seen that the double optical probe device such as described above provides for the determination of the refractive index $n_{lo}$ of a liquid reduced to the reference temperature $T_o$, in accordance with an error which turns out to be more positive than the negative error inherent to the use of a single probe device, provided the following conditions are satisfied:

$$k_1 > k_2$$

and $$q_1 < q_2 \text{ (or } dn_{p1}/dT > dn_{p2}/dt)$$

This error E can, however, be practically cancelled by choosing the respective parameters $k_1$, $k_2$, $q_1$, $q_2$ so that they obey the relation:

$$k_1 q_1 \approx k_2 q_2$$

which then makes it possible to obtain a measuring device which is almost perfectly temperature compensated.

This error E can, in addition, in certain desired cases, be made to be positive through an appropriate choice of the respective parameters $k_1$, $k_2$, $q_1$ and $q_2$, which then makes it possible to obtain a temperature overcompensated device (which is impossible with single probe devices).

Using a device of the type shown in FIG. 4 and in which the optical probe 51 was made of polystyrene (refractive index (n=1.6)) and the optical probe 52 was made of glass (n+1.47), a comparative test was carried out, the result of which was as follows:

(a) for each probe considered separately, the temperature sensitivity was:

for probe 51 $(dn/dT) = -1.55 \cdot 10^{-4}/°C.$ for probe 52 $(dn/dT) = -2.74 \cdot 10^{-4}/°C.)$ (b) by using the entire device as illustrated in FIG. 4, the temperature sensitivity became equal to $$dn/dT = -0.073 \cdot 10^{-6}/°C.)$$

which value is much lower than those mentioned above, which confirms the temperature compensation capacity of the device according to FIG. 4.

I claim:

1. A double optical probe device for the determination of the refractive index of a liquid reduced to a predetermined reference temperature, said device being adapted to give rise to an error which is more positive than the negative error inherent to a single optical probe device, characterized by the fact that said device comprises:

a first and second optical probe each consisting of a light conducting body comprising an inlet section and an outlet section connected to each other by an intermediate section, at least said intermediate section of each of said probes being designed to be immersed in said liquid, and this intermediate section being, furthermore, adapted to convey light between said inlet section and said outlet section by giving rise to a quantity of light emerging from said outlet section of each of said probes which varies linearly as a function of the refractive index of said liquid, at least one source of light associated with said inlet section of said first and second probes, for the injection of a quantity of predetermined light into each of these inlet sections, and means associated with said outlet section of said first and second probes, for the elaboration of a resulting signal corresponding to the difference in the quantities of light respectively emerging from said outlet sections, said intermediate sections of said first and second probes being, in addition, chosen, on the one hand, as regards their geometric arrangement, so as to have respective sensitivities "$m_1$" and "$m_2$" relative to the variations in the refractive index of the liquid which are such that "$m_1$" is greater than "$m_2$" and, on the other hand, as regards the constituent material thereof, so as to have apparent respective sensitivities "$q_1$" and "$q_2$" relative to the variations in temperature of this liquid which are such that "$q_1$" is lower than "$q_2$", so that said resulting signal elaborated at the outlet of said probes constitutes a signal which is representative of said refractive index of the liquid reduced to said reference temperature, the refractive index thus determined being, furthermore, tainted, for temperatures that are different from this reference temperature, with an error which is more positive than that which would result from the use of a single probe.

2. A device according to claim 1 characterized in that each of said intermediate sections consists of a prism comprising at least two reflecting surfaces, provided so as to successively reflect at least a part of the light originating from said inlet section up to said outlet section of each of said bodies.

3. A device according to claim 1, designed to provide a substantially perfect temperature compensation, characterized in that the geometric arrangement as well as the constituent material of each of said intermediate sections of said probes are chosen so as to have, respectively, respective effective sensitivities "$m_1$" and "$m_2$" relative to the variations in the refractive index of the liquid, as well as respective apparent sensitivities "$q_1$" and "$q_2$" relative to the variations in temperature of that liquid, which substantially obey the relation: $m_1 q_1 = m_2 q_2$.

4. A double optical probe device for the determination of the refractive index of a liquid reduced to a predetermined reference temperature, said device being adapted to give rise to an error which is more positive than the negative error inherent to a single optical probe device, characterized in that said device comprises:

a first and second optical probe each consisting of a light conducting body comprising an inlet section and an outlet section connected to each other by an intermediate section, at least said intermediate section of each of said probes being designed to be immersed in said liquid, and this intermediate section being, furthermore, adapted to convey light between said inlet section and said outlet section by giving rise to a quantity of light emerging from said outlet section of each of said probes which varies exponentially as a function of the refractive index of said liquid, at least one light source associated with said inlet section of said first and second probes, for the injection of a predetermined quantity of light into each of these inlet sections, and means associated with said outlet section of said first and second probes, for the elaboration of a resulting signal corresponding to the quotient of light quantities respectively emerging from said outlet sections, said intermediate sections of said first and second probes being, in addition, chosen, on the one hand, as regards their geometric arrangement, so as to have respective exponentiality coefficients "$k_1$" and "$k_2$" relative to the variations of the refractive index of the liquid such that "$k_1$" is higher than "$k_2$", and, on the other hand, as regards the constituent material thereof, so as to have apparent respective sensitivities "$q_1$" and "$q_2$", relative to the variations in temperature of this liquid such that "$q_1$" is lower than "$q_2$", so that said resulting signal elaborated at the outlet of said probes constitutes a signal which is representative of said refractive index of the liquid reduced to said reference temperature, the refractive index thus determined being, furthermore, tainted, for temperatures differing from this reference temperature, with an error which is more positive than that which would result from the use of a single probe.

5. A device according to claim 4, characterized in that each of said intermediate sections consists of a curved longilinear section the curvature of which is sufficiently pronounced to give rise to a non negligible passage of light in the liquid through refraction, said inlet and outlet sections to which is connected each of the intermediate sections being longlinear as well.

6. A device according to claim 4 designed to provide a substantially perfect temperature compensation, characterized in that the geometric arrangement as well as the constituent material of said curved intermediate sections are chosen so as to have, respectively, respective exponentiality coefficients "$k_1$" and "$k_2$" relative to the variations in the refractive index of the liquid, as well as respective apparent sensitivities "$q_1$" and "$q_2$" relative to variations in temperature of this liquid, which substantially obey the relation: $k_1 q_1 = k_3 q_2$.

* * * * *